United States Patent
Nakaya et al.

(10) Patent No.: US 8,449,822 B2
(45) Date of Patent: May 28, 2013

(54) SMEAR PREPARING APPARATUSES AND METHODS OF PREPARING SAMPLE SMEARS

(75) Inventors: Masanori Nakaya, Kobe (JP); Toshio Watanabe, Oonojo (JP); Yoshiyuki Tamura, Kobe (JP)

(73) Assignee: Sysmex Corporation, Kobe (JP)

( * ) Notice: Subject to any disclaimer, the term of this patent is extended or adjusted under 35 U.S.C. 154(b) by 834 days.

(21) Appl. No.: 11/407,518

(22) Filed: Apr. 20, 2006

(65) Prior Publication Data

US 2006/0263249 A1 Nov. 23, 2006

Related U.S. Application Data

(63) Continuation-in-part of application No. 10/903,374, filed on Jul. 30, 2004, now abandoned, and a continuation-in-part of application No. 10/345,302, filed on Jan. 16, 2003, now Pat. No. 7,368,080.

(30) Foreign Application Priority Data

Jan. 18, 2002 (JP) .................................. 2002-10181
Jul. 31, 2003 (JP) ................................. 2003-204711

(51) Int. Cl.
*G01N 33/487* (2006.01)
*G01N 33/48* (2006.01)
*G01N 33/49* (2006.01)

(52) U.S. Cl.
USPC ................ 422/63; 422/67; 422/68.1; 436/43; 436/46; 436/174

(58) Field of Classification Search
USPC .................... 422/100, 63, 67, 68.1, 500–501, 422/509, 519; 436/43, 174
See application file for complete search history.

(56) References Cited

U.S. PATENT DOCUMENTS

| | | |
|---|---|---|
| 4,041,995 A | 8/1977 | Columbus |
| 4,108,608 A | 8/1978 | Maher, Jr. et al. |
| 4,378,333 A | 3/1983 | Laipply |
| 5,089,229 A | 2/1992 | Heidt et al. |
| 5,209,903 A | 5/1993 | Kanamori et al. |
| 5,356,595 A | 10/1994 | Kanamori et al. |
| 5,573,727 A | 11/1996 | Keefe |
| 5,650,332 A | 7/1997 | Gao et al. |
| 5,665,312 A | 9/1997 | Sperber et al. |
| 5,766,549 A | 6/1998 | Gao et al. |
| 5,779,982 A | 7/1998 | Aota et al. |

(Continued)

FOREIGN PATENT DOCUMENTS

| | | |
|---|---|---|
| EP | 1 271 125 A2 | 1/2003 |
| EP | 1 271 125 A3 | 6/2004 |
| JP | 63-217273 | 9/1988 |

*Primary Examiner* — Brian R Gordon
(74) *Attorney, Agent, or Firm* — Brinks Hofer Gilson & Lione

(57) ABSTRACT

Smear preparing apparatuses for preparing a smear of a specimen on a glass slide are described that include a memory for storing smearing conditions in connection with pertinent information required for establishing the smearing condition; and a controller for retrieving one of the stored smearing conditions corresponding to the pertinent information of the specimen from the memory and for determining it as the smearing condition of the specimen. Methods of preparing sample smears on a glass slide are also described that include receiving condition identification data; storing smear preparing conditions correlated with the condition identification data; retrieving the smear preparing conditions correlated with the condition identification data; and applying the sample smear to the glass slide based on the smear preparing conditions.

10 Claims, 8 Drawing Sheets

U.S. PATENT DOCUMENTS

| | | | |
|---|---|---|---|
| 5,804,145 A | 9/1998 | Gao et al. | |
| 5,854,075 A | 12/1998 | Levine et al. | |
| 5,871,696 A | 2/1999 | Roberts et al. | |
| 5,948,359 A | 9/1999 | Kalra et al. | |
| 5,958,760 A | 9/1999 | Freeman | |
| 5,985,669 A | 11/1999 | Palander | |
| 6,045,759 A | 4/2000 | Ford et al. | |
| 6,083,759 A | 7/2000 | Teshima | |
| 6,127,184 A | 10/2000 | Wardlaw | |
| 6,258,322 B1 | 7/2001 | Meikle | |
| 6,319,470 B1 | 11/2001 | Lefevre et al. | |
| 6,387,326 B1 | 5/2002 | Edwards et al. | |
| 6,495,106 B1 | 12/2002 | Kalra et al. | |
| 6,585,936 B1 | 7/2003 | Shah | |
| 6,673,315 B2 | 1/2004 | Sheridan et al. | |
| 6,703,247 B1 | 3/2004 | Chu | |
| 6,735,531 B2 | 5/2004 | Rhett et al. | |
| 6,869,570 B2 | 3/2005 | Wardlaw | |
| 2002/0110494 A1 | 8/2002 | Lemme et al. | |
| 2003/0003022 A1 | 1/2003 | Tamura et al. | |
| 2003/0099573 A1 | 5/2003 | Tseung et al. | |
| 2003/0099580 A1 | 5/2003 | Pressman et al. | |
| 2003/0138355 A1 | 7/2003 | Tamura et al. | |
| 2004/0033169 A1 | 2/2004 | Shah | |
| 2004/0086428 A1 | 5/2004 | Loeffler et al. | |
| 2005/0025672 A1 | 2/2005 | Nakaya et al. | |

| HCT | Smear-ing level | Smearing control condition | | | |
|---|---|---|---|---|---|
| | | Speed (mm/sec) | Angle (°) | Fitting time (sec) | Amount of dispensed sample (μL) |
| Less than 20 | 1 | 135 | 20 | 3.0 | 4 |
| 20 - 30 | 2 | 120 | 17 | 2.0 | 4 |
| 30 - 40 | 3 | 105 | 17 | 2.0 | 3 |
| 40 - 50 | 4 | 90 | 15 | 2.0 | 3 |
| Not less than 50 | 5 | 75 | 13 | 2.0 | 2 |
| | 6 | 120 | 15 | 2.0 | 3 |
| | 7 | 90 | 17 | 3.0 | 4 |
| | 8 | 105 | 17 | 2.0 | 4 |
| | 9 | 110 | 15 | 2.0 | 3 |
| | 10 | 90 | 20 | 3.0 | 3 |

Fig. 13

| Smearing level | WBC | RBC | Abnormal message | Medical information |
|---|---|---|---|---|
| 6 | 40<WBC<70 | 300<RBC<500 | Nothing | Nothing |
| 7 | 40<WBC<70 | 300<RBC<500 | Nothing | Paediatics |
| 8 | 70<WBC<120 | 10<RBC<20 | Lymphopenia | Leukemia |
| 9 | 70<WBC<120 | 10<RBC<20 | Lymphocytosis | Leukemia |
| 10 | 40<WBC<70 | 500<RBC<700 | Neutropenia | Leukemia |

SMEAR PREPARING APPARATUSES AND METHODS OF PREPARING SAMPLE SMEARS

RELATED APPLICATIONS

This application is a continuation-in-part of prior application Ser. No. 10/903,374, filed Jul. 30, 2004, now abandoned which claims priority under 35 U.S.C. §119 to Japanese Patent Application No 2003-204711, filed Jul. 31, 2003, and a continuation-in-part of prior application Ser. No. 10/345,302, U.S. Pat. No. 7,368,080, filed Jan. 16, 2003, which claims priority under 35 U.S.C. §119 to Japanese Patent Application No. 2002-10181, filed Jan. 18, 2002. The entire contents of all four of the above-identified documents are hereby incorporated herein by reference.

FIELD OF THE INVENTION

The present invention relates to a smear preparing apparatus for preparing a smear of sampled blood, bone-marrow fluid and the like.

BACKGROUND

Conventionally, in order to observe blood or the like by a microscope or similar apparatus, a smear preparing apparatus in which blood or the like is dropped on a glass slide and smeared by a spreader glass (smearing member) to generate a smear is used.

Since each sample has different characteristics such as particle density, viscosity and the like, if the smear is always generated under the same condition, the smear is unsuitable for observation in some samples.

Therefore, there is known a smear preparing apparatus in which the smearing conditions are established for each sample based on a measurement result from a blood analyzer (refer to U.S. Pat. No. 5,209,903).

According to such a conventional apparatus, the smearing condition is determined based, for example, on a hematocrit value. In addition, since it is known that blood viscosity generally increases as the amount of hemoglobin increases, it is possible to establish the smearing condition based on the measurement result of the hemoglobin amount.

In addition, although the method of setting the smearing condition by the above-described conventional apparatus is very effective when the smear is automatically generated, it does not address the case of special samples or various kinds of user's needs.

For example, although the hematocrit value of a leukemia patient is normal or relatively small, it has been found that the WBC (White Blood Cell) of the leukemia patient is weak and liable to be destroyed.

When a blood smear of such a patient is made, it is necessary to make it thicker than the smear made under smearing conditions based on the normal hematocrit value when the blood on the slide glass is smeared by the spreader glass, so as not to destroy the WBC.

In addition, observers who observe the smear by a microscope have different demands for the smear. That is, some observers want to observe a widely spread smear having a small thickness, while some observers want to observe the smear thickly collected in a small region.

SUMMARY

The scope of the present invention is defined solely by the appended claims, and is not affected to any degree by the statements within this summary.

A first smear preparing apparatus for preparing a sample smear on a glass slide comprises: (a) an information acceptor configured for receiving condition identification data; (b) a memory coupled to the information acceptor and configured for storing smear preparing conditions correlated with the condition identification data; (c) a spreader glass driving mechanism coupled to the memory and configured for applying the sample smear to the glass slide based on the smear preparing conditions; and (d) a controller coupled to the spreader glass driving mechanism and configured for retrieving from the memory the smear preparing conditions that correspond to the condition identification data received by the information acceptor, and for controlling the spreader glass driving mechanism, wherein the sample smear is prepared according to the smear preparing conditions retrieved by the controller.

A second smear preparing apparatus for preparing a sample smear on a slide glass comprises: (a) means for obtaining sample identification data; (b) an information transmitter coupled to the means for obtaining sample identification data and configured for transmitting the sample identification data to a computer; (c) an information acceptor coupled to the computer and configured for receiving condition identification data correlated with the sample identification data; (d) an input unit coupled to the computer and configured for inputting smear preparing conditions that correlate with the condition identification data; (e) a memory coupled to the computer and configured for storing the smear preparing conditions; (f) a spreader glass driving mechanism coupled to the computer and configured for applying the sample smear to the glass slide based on the smear preparing conditions; and (g) a controller coupled to the computer and configured for retrieving from the memory the smear preparing conditions that correspond to the condition identification data received by the information acceptor, and for controlling the spreader glass driving mechanism, wherein the sample smear smear is prepared according to the smear preparing conditions retrieved by the controller.

A method of preparing a sample smear on a glass slide comprises: (a) receiving condition identification data; (b) storing smear preparing conditions correlated with the condition identification data; (c) retrieving the smear preparing conditions correlated with the condition identification data; and (d) applying the sample smear to the glass slide based on the smear preparing conditions.

BRIEF DESCRIPTION OF THE DRAWINGS

FIG. 13 is a table showing a setting example of the smearing level information.

DETAILED DESCRIPTION

By way of introduction, the present invention provides in some embodiments a smear preparing apparatus capable of establishing the smearing conditions on the basis of pertinent information (diagnostic information and the like) for establishing smearing conditions.

In some embodiments, the present invention provides a smear preparing apparatus capable of establishing smearing conditions on the basis of not only the measurement results from the analyzer but also other diagnostic information.

In some embodiments, the present invention provides a smear preparing apparatus capable of establishing smearing conditions for easy observation based on an observer's preference.

A smear preparing apparatus embodying features of the present invention prepares a smear of a specimen on a glass slide by using a spreader based on a smearing condition. In some embodiments, the apparatus comprises: a memory for storing smearing conditions in connection with pertinent information required for establishing the smearing condition; and a controller for retrieving one of the stored smearing conditions corresponding to the pertinent information of the specimen from the memory and for determining it as the smearing condition of the specimen.

Hereinafter, an embodiment of a smearing preparing system is described with reference to the drawings.

Figure 1:
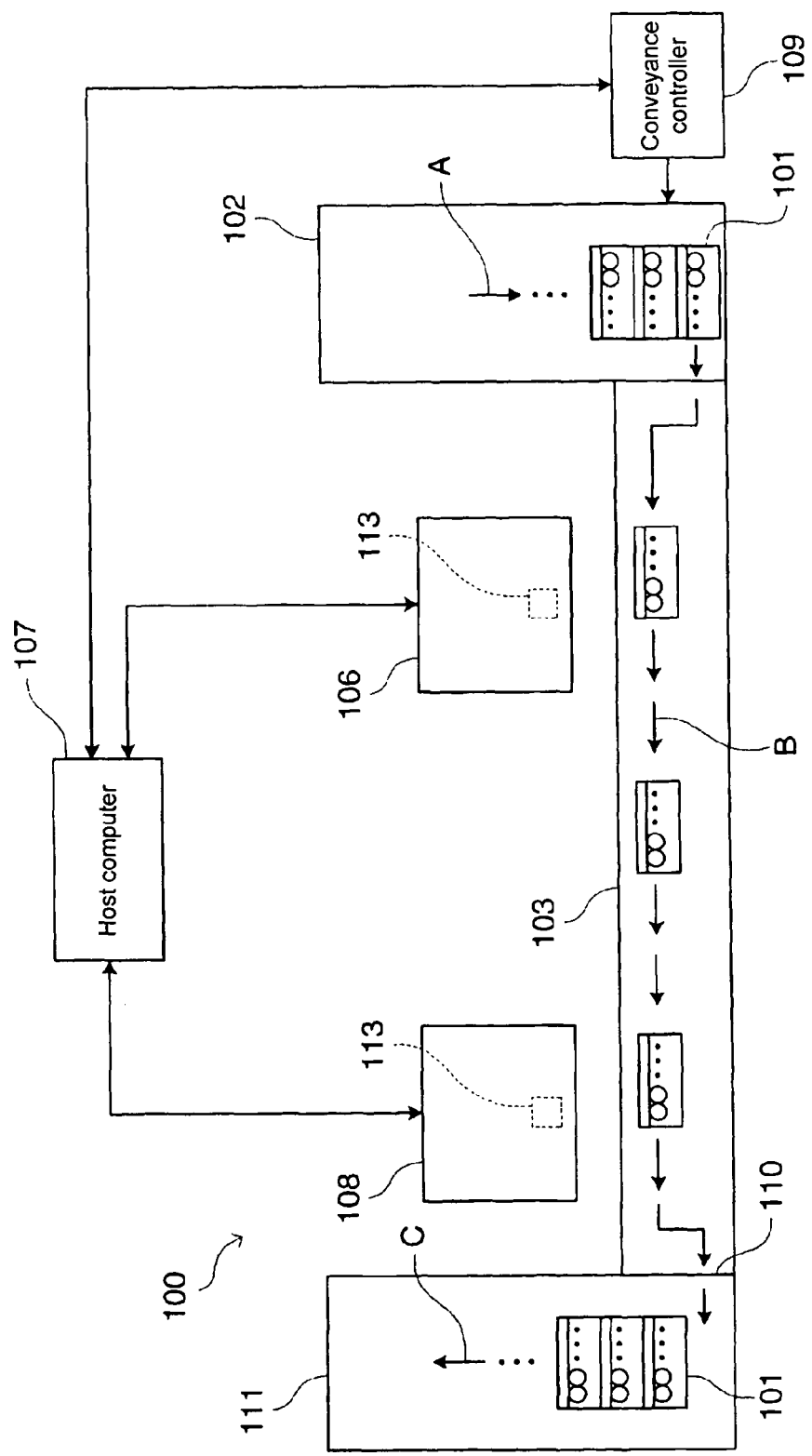
FIG. 1 is a schematic view of a smear preparing system embodying features of the present invention.

FIG. 1 is a plan view showing a smear preparing system.

As shown in FIG. 1, a system 100 comprises a loader 102, a conveyer 103, and unloader 111. A blood analyzer 106 and a smear preparing apparatus 108 are arranged along the conveyer 103.

A conveyance controller 109 for controlling the loader 102, the conveyer 103 and the unloader 111 is provided and a host computer 107 which exchanges information or instructs among the blood analyzer 106, the smear preparing apparatus 108 and the conveyance controller 109 or gives instructions to them is provided.

Figure 2:
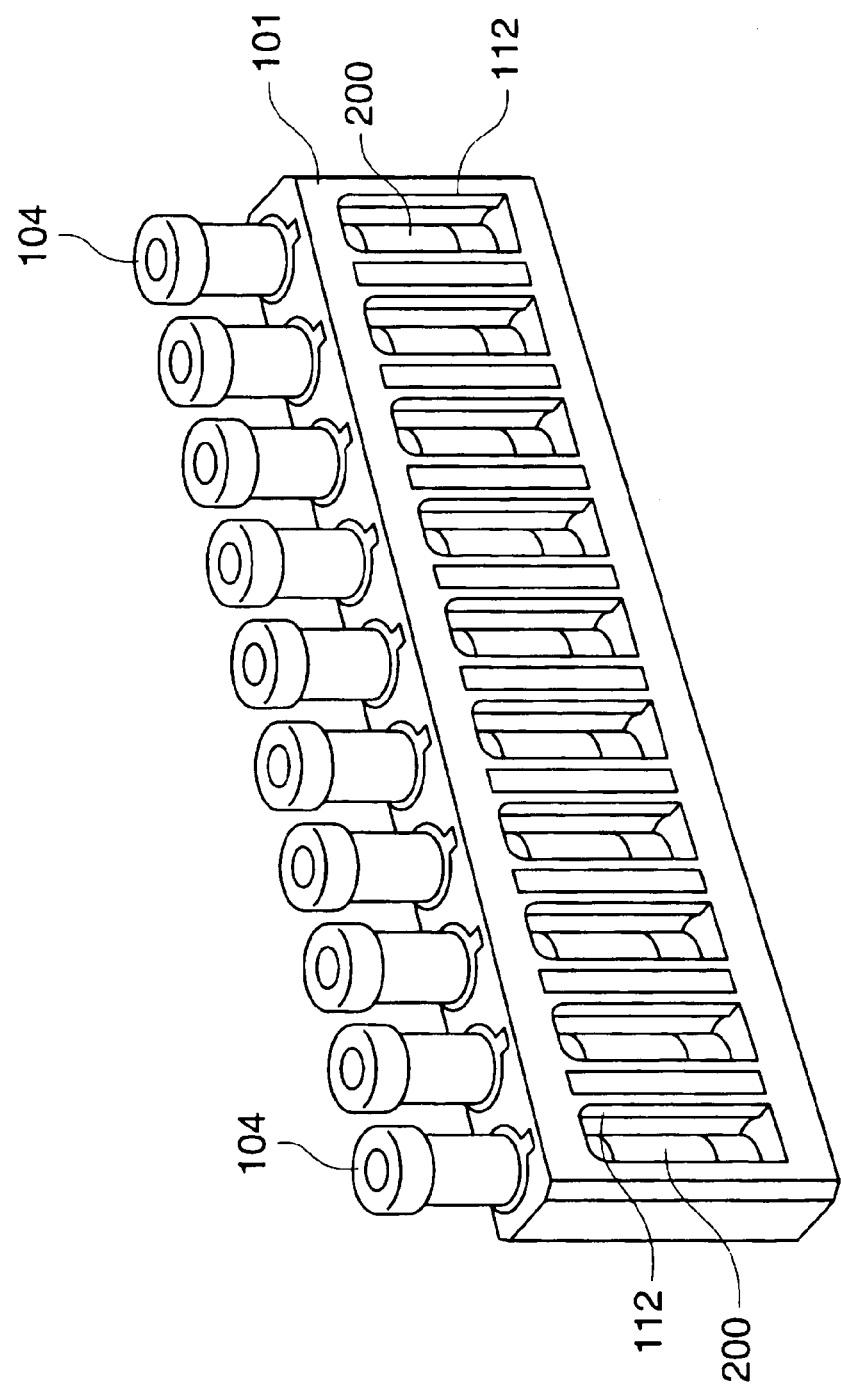
FIG. 2 is a perspective view of a sample rack.

A plurality of sample racks 101 are put on the loader 102. The sample racks 101 are conveyed to a carry-in end of the conveyer 103 adjacent to the loader 102 in the direction shown by an arrow A and then exit the loader 102. As shown in FIG. 2, each sample rack 101 has a plurality of sample containers 104 which contain blood samples.

The sample racks 101 are conveyed by the conveyer 103 in the direction of an arrow B and reach a discharge end 110 of the conveyer 103 through the blood analyzer 106 and the smear preparing apparatus 108. Then, the sample racks 101 are conveyed in the direction of arrow C by the unloader 111 adjacent to the discharge end 110 of the conveyer 103.

In addition, as shown in FIG. 2, a barcode label 200 showing identification information (ID) of the sample is attached on each sample container 104. Windows 112 are provided on the longitudinal side of the sample rack 101 through which the barcode on the sample container 104 is read.

When the sample rack 101 containing the sample containers 104 is put on the loader 102, the system 100 is started. Then, the first sample rack 101 is moved in the direction of the arrow B by the conveyer 103 and stops at the blood analyzer 106.

Here, the barcode of the first sample container 104 is read by a barcode reader 113. The blood analyzer 106 analyzes the sample in the sample container 104 and reports the analyzed result to the host computer 107 together with the barcode information. The blood analyzer 106 repeats the above operations until samples of all sample containers 104 are analyzed. The host computer 107 determines whether it is necessary to prepare the smear for that sample or not based on the analyzed result.

Then, the sample rack 101 having only the samples whose smear no longer needs to be prepared passes through the smear preparing apparatus 108 on the conveyer 103 which is controlled by the conveyance controller 109 based on a command of the host computer and reaches the unloader 111. The sample rack 101 containing the sample whose smear needs to be prepared is moved to reach the smear preparing apparatus 108 by the conveyer 103 which is controlled by the conveyance controller 109 based on the command of the host computer 107. The barcode of each sample container 104 is read by the barcode reader 113 of the smear preparing apparatus 108 and transmitted to the host computer 107. When the host computer 107 determines that the smear needs to be prepared, the smear preparing apparatus 108 takes a sample whose smear needs to be prepared from the sample container 104 and prepares a blood smear for it. Meanwhile, the sample container 104 whose smear no longer needs to be prepared is moved further in the direction of the arrow B and the next sample container 104 reaches the smear preparing apparatus 108.

Then, the sample rack 101 which passed through the smear preparing apparatus 108 on the conveyer 103 reaches the unloader 111.

Figures 3, 4:
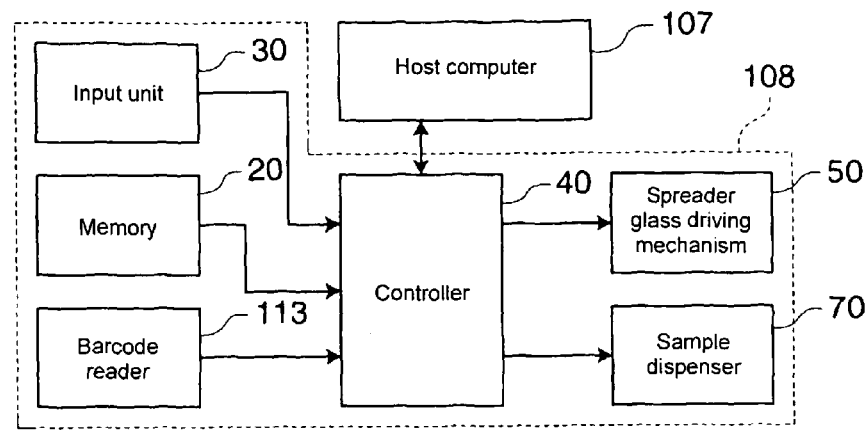
FIG. 3 is a block diagram showing a smear preparing apparatus embodying features of the present invention.
FIG. 4 is a table showing relations between smearing levels and a smearing control condition.

FIG. 3 is a block diagram of the smear preparing apparatus 108. The smear preparing apparatus 108 comprises a memory 20, an input unit 30, a controller 40, a sample dispenser 70, a spreader glass driving mechanism 50 and a barcode reader 113.

The controller 40 comprises a CPU, a ROM and a RAM, and the input unit 30 comprises a keyboard.

Smearing control conditions are set so as to correspond to smearing levels (condition identification data) through the input unit 30 and stored in the memory 20. The smearing control conditions are previously stored before the smearing is actually performed.

FIG. 4 is a table showing relations between the smearing levels and smearing control conditions stored in the memory 20.

As shown in FIG. 4, each of the smearing levels 1 to 10 corresponds to the smearing control conditions such as a speed (movement speed of a spreader glass), an angle (which is formed between the spreader glass and a slide glass), a fitting time (after the spreader glass comes in contact with sample dispensed on the slide glass until the spreader glass starts to move), and the like. In addition, the smearing control condition may comprise smearing starting position on the slide glass and the like.

As shown in FIG. 4, referring to the smearing levels 1 to 5, default values are previously set for the corresponding smearing control conditions and a range of HCT (Hematocrit value) corresponds to each of the levels. The default values are also set for the ranges of HCT. The relation between the HCT and the smearing level is used when the host computer 107 does not designate the smearing level to the controller 40 as will be described below. Referring to the smearing levels 6 to 10, the corresponding smearing control conditions are arbitrarily set by a user. In addition, according to the smearing levels 1 to 5, the corresponding smearing control conditions and the HCT ranges may be arbitrarily set by the user.

The controller 40 reads the corresponding smearing control conditions from the memory 20 when the host computer 107 designates the smearing level, and controls the spreader glass driving mechanism 50 and the sample dispenser 70 based on the read smearing control conditions (a speed, an angle, a fitting time and a dispensed amount) to prepare the smear.

Figure 5:
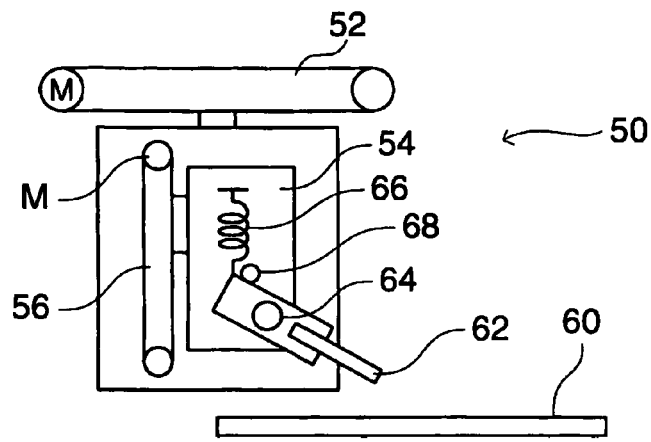
FIG. 5 is a schematic diagram showing a driving mechanism for a spreader glass.

FIG. 5 is a view showing a schematic constitution of the spreader glass driving mechanism 50 in the smear preparing apparatus 108. The spreader glass driving mechanism 50 comprises a back-and-forth driving mechanism 52 which moves the spreader glass 62 parallel to the surface of the slide glass 60, a vertical driving mechanism 56 which elevates the spreader glass to and from the slide glass 60, and an angle retaining mechanism 54 which retains the angle formed between the spreader glass 62 and the slide glass 60. The back-and-forth driving mechanism 52 and the vertical driving mechanism 56 are provided for moving the spreader glass 62 back and forth, and up and down, and each comprises a belt-motor mechanism provided with a motor M and a belt.

According to the back-and-forth driving mechanism 52, a moving speed of the spreader glass 62 can be adjusted by a rotation speed of the belt motor.

In addition, the angle retaining mechanism 54 comprises an elastic member 66 which pulls the spreader glass 62 so as to be rotated around a spindle 64, and a stopper 68 which fixes a limit of rotation, in which after an end of the spreader glass comes in contact with the slide glass 60, it is further lowered so that the angle formed with the slide glass 60 is changed.

Figure 6:
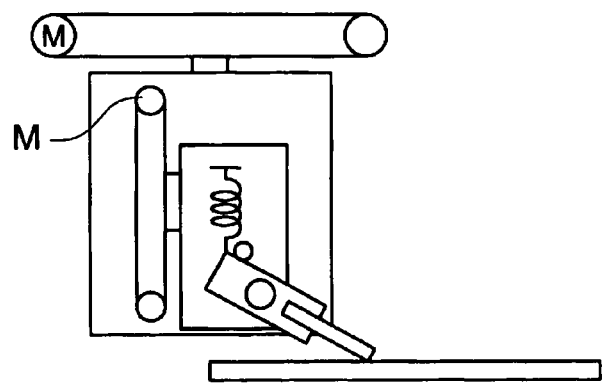
FIG. 6 is a schematic diagram showing operation of the driving mechanism of FIG. 5.
Figure 7:
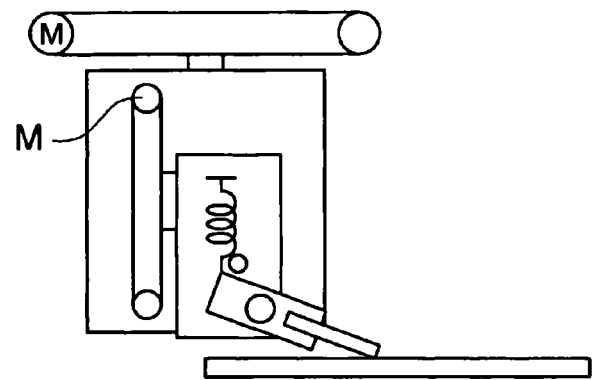
FIG. 7 is schematic diagram showing operation of the driving mechanism of FIG. 5.

FIG. 6 is a view showing a state in which the angle between the spreader glass 62 and the slide glass 60 is kept large by the angle retaining mechanism 54 and FIG. 7 is a view showing a state in which the angle is kept small. The angle formed between the spreader glass 62 and the slide glass 6 is adjusted by an expansion state of the elastic member 66.

Figure 8:
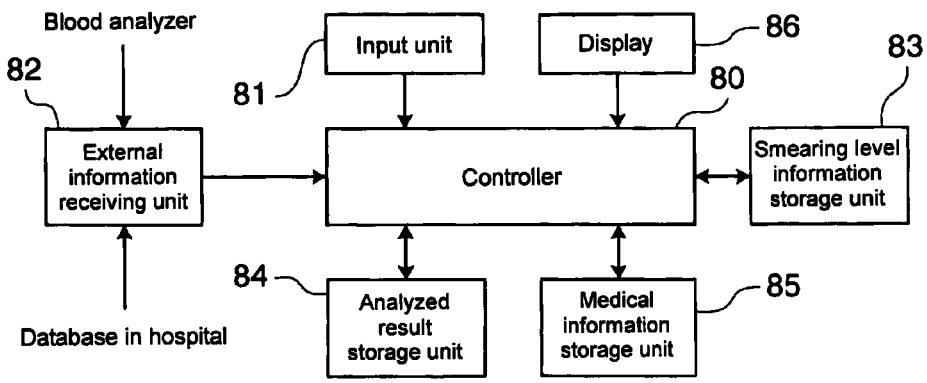
FIG. 8 is a block diagram showing a host computer.

FIG. 8 is a block diagram showing the host computer 107. A controller 80 stores information set related with the smearing levels through an input unit 81, in a smearing level information storage unit 83 and receives the analyzed result from the blood analyzer 106 (FIG. 1) through an external information receiving unit 82 and stores it in an analyzed result storage unit 84 together with barcode (ID) information.

The controller 80 further receives medical information and ID information of sample donors from an external terminal (not shown) through the external information receiving unit 82 and stores them in a medical information storage unit 85. A display 86 displays items or contents set and input from the input unit 81 by the user.

The controller 80 comprises a CPU, a ROM, and a RAM. The input unit 81 comprises a keyboard, the display 86 comprises an LCD, the external information receiving unit 82 comprises an I/O port, and each of the storage units 83 to 85 comprises a RAM.

Figure 9:
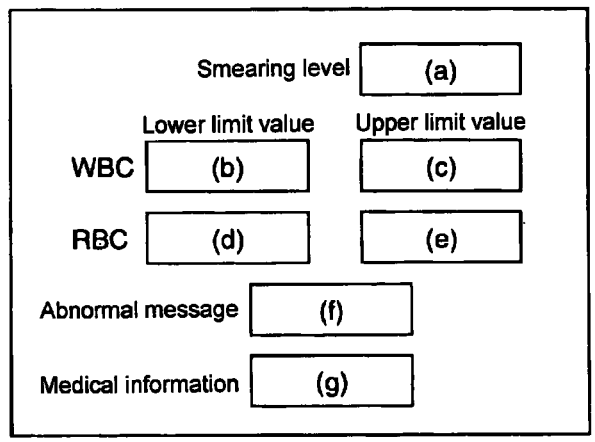
FIG. 9 is a view of a screen showing smearing level information.

FIG. 9 shows an example of a screen displayed in the display 86 when the user sets the smearing level information from the input unit 81.

Referring to FIG. 9, any one of smearing levels 1 to 10 (FIG. 4) is previously set in column (a), an upper limit value and a lower limit value of WBC (White Blood Cell) count are previously set in columns (b) and (c), an upper limit value and a lower limit value of RBC (Red Blood Cell) count are previously set in columns (d) and (e), and an abnormal message and medical information are previously set in columns (f) and (g).

In addition, the abnormal message comprises "WBC abnormal", "neutropenia", "neutrophilia", "lymphopenia", "lymphocytosis", "RBC abnormal", "anemia", "RBC agglutination", "HGB defect", "PLT abnormal" and the like which are expected to be transmitted with numeric values of analytical item to the host computer 107 from the blood analyzer 106, and one or more of them are selected and set in the column (f).

In addition, the medical information comprises personal information (age, gender, history of disease, name of in-patients ward) and diagnostic information (name of disease, disease state, examination items) of the expected sample donor (patient), one or more of them are selected and set in the column (g).

Figure 10:
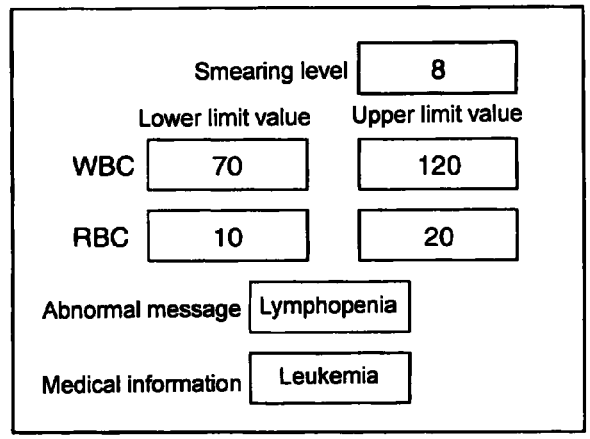
FIG. 10 is a view of a screen showing smearing level information.

FIG. 10 shows an example of a screen in which the setting is completed. In addition, a column in which the setting is not performed is left blank.

FIG. 13 shows a table formed by setting the smearing level information through the user in FIG. 9, which is stored in the smearing level information storage unit 83.

When the host computer 107 receives the barcode information (ID) from the smear preparing apparatus 108, searches the analyzed result and the medical information which correspond to the ID information from the storage units 84 and 85 and when there is a corresponding one in the table shown in FIG. 13, indicates the corresponding smearing level to the smear preparing apparatus 108. If there is not corresponding one, the HCT value is transmitted to the smear preparing apparatus 108 from the analyzed result corresponding to the ID information.

A series of operations of the smear preparing system 100 is described with reference to flowcharts in FIGS. 11 and 12.

Figure 11:
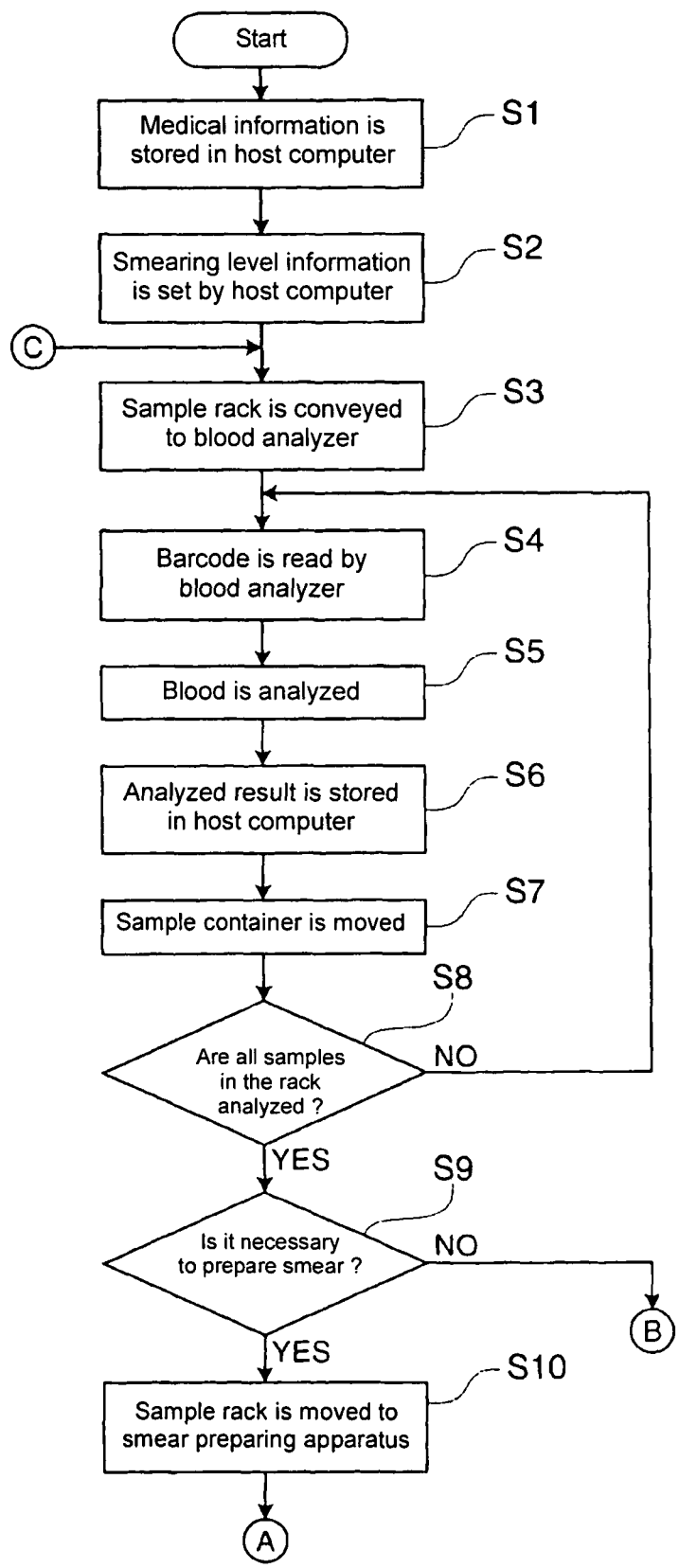
FIG. 11 is a flowchart showing operations of a smear preparing system embodying features of the present invention.

Referring to FIG. 11, the medical information of the sample donor (patient) is transmitted to the host computer 107 from a database in a hospital, for example and stored therein at step S1.

Then, the smearing level information is set by the host computer 107 as shown in FIGS. 9 and 10 at step S2. Sample containers 104 (FIG. 2) having the samples are mounted on the sample rack 101 and set on the loader 102.

When the system 100 is started, the loader 102 and the conveyer 103 are driven by the conveyance controller 109 and the sample rack 101 is conveyed to the blood analyzer 106 at step S3. The barcode of the first sample container 104 is read and the sample is extracted from the sample container 104 and analyzed at step S5. The analyzed result (analyzed numeric value of each item and the abnormal message determined from the numeric value) is transmitted to the host computer 107 at step S6. The analyzed sample container 104 is moved by a predetermined distance (an arrangement pitch of the containers 104) at step S7. When there is any unanalyzed sample container 104 in the sample rack 101 at step S8, the operation returns to step S4 and the barcode of the unanalyzed sample container 104 is read by the blood analyzer 106. When all samples are analyzed at step S8, the operation proceeds to step S9. When the smear does not need to be generated from any of the samples in the sample rack 101 at step S9, the sample rack 101 is conveyed to the unloader 111. When it is necessary to prepare the smear at step S9, the analyzed sample rack 101 is conveyed to the smear preparing apparatus 108 at step S10.

Figure 12:
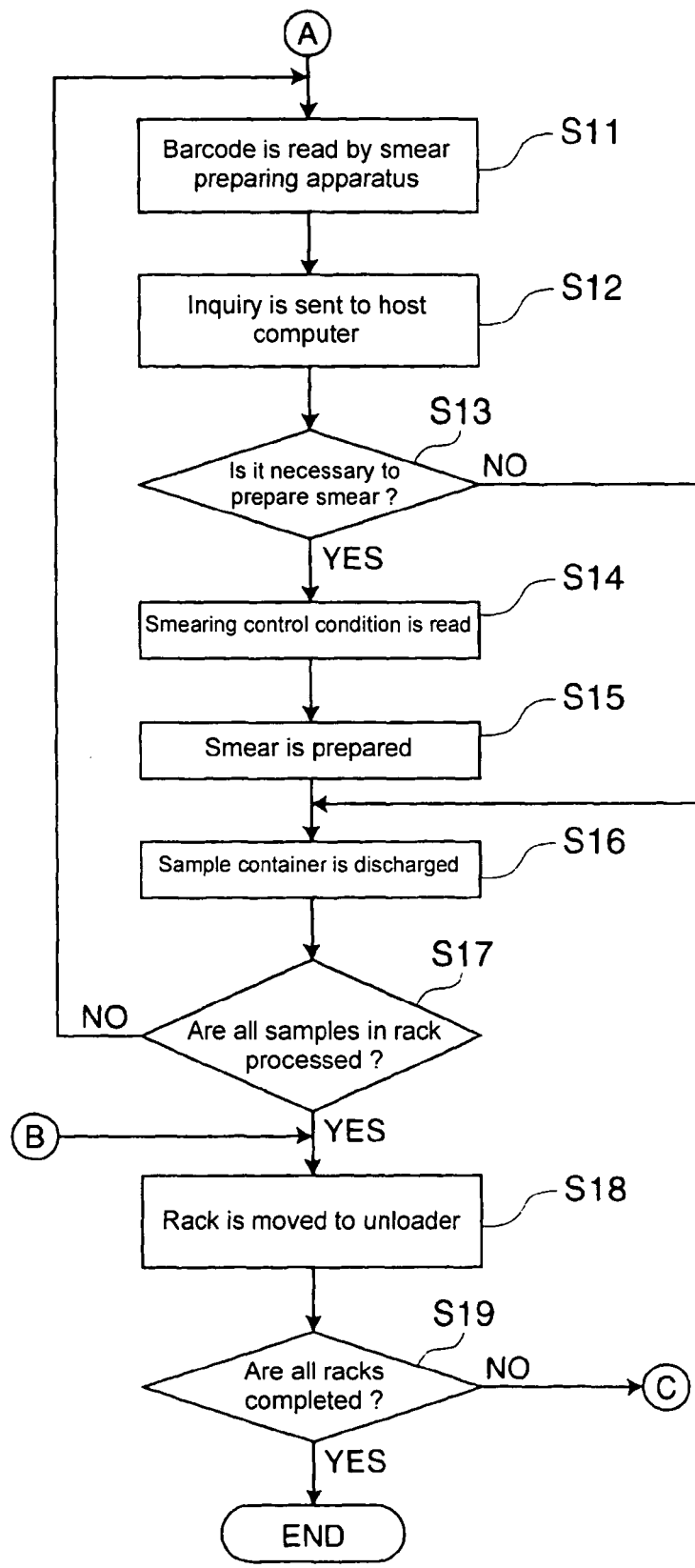
FIG. 12 is a flowchart showing operations of a smear preparing system embodying features of the present invention.

Then, as shown in FIG. 12, the barcode of the first sample container 104 is read in the smear preparing apparatus 108 at step S11. The smear preparing apparatus 108 inquires of the host computer 107 about the sample of the barcode at step S12. When the host computer 107 determines that it is necessary to prepare the smear, it indicates the smearing level when the smearing level is designated, or indicates the HCT value when the smearing level is not designated, to the smear preparing apparatus 108, and the controller 40 of the smear preparing apparatus 108 reads the smearing control conditions corresponding to the smearing level or the HCT value from the memory 20 at steps S13 and S14. As shown in FIG. 4, the table in which the relations between the smearing levels, the HCT values, and the smearing control conditions are previously set is stored in the memory 20 and the controller 40 reads the smearing control conditions from the memory 20 based on the table. The case where it is necessary to generate the smear is a case where the analyzed result of the sample by the blood analyzer 106 contains the abnormal message, for example. The smear is prepared according to the read smearing control conditions at step S15.

Then, the sample container 104 whose smear is made is moved by the predetermined distance (arrangement pitch of the containers 104) at step S16 and when all samples in the sample rack 101 are processed, the sample rack 101 is moved to the unloader 111 at steps S17 and S18. In step S17, when there is any unprocessed sample container 104, the operation returns to step S11 and its barcode is read in the smear preparing apparatus 108. In addition, when it is determined that it is not necessary to make the smear at step S13, the sample container 104 is moved by the predetermined distance at step S16. The case where it is not necessary to make the smear is a case where the analyzed result of the sample by the blood analyzer 106 does not contain the abnormal message, for example.

When all of the sample racks are not processed yet at step S19, the operation proceeds to step S3.

As the smearing control condition, at least one selected from a dispensed amount of the sample to the slide glass, an angle of the smearing member to the slide glass, a moving speed of the smearing member to the slide glass, a fitting time of the sample to the smearing member, and smearing starting position to the slide glass can be used.

The foregoing detailed description and accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

The invention claimed is:

1. A smear preparing system comprising:
   a host computer which is coupled with a blood sample analyzer via a network and which obtains a plurality of analysis results of a blood sample from the blood sample analyzer, the analysis results including a hematocrit value; and
   a smear preparing apparatus coupled with the host computer via a network for preparing a sample smear on a glass slide, the smear preparing apparatus comprising:
      a spreader glass;
      a spreader glass driving mechanism comprising a motor and configured for preparing a sample smear on a glass slide by moving the spreader glass on the glass slide;
      a memory storing smear preparing conditions in association with at least ranges of hematocrit values and storing at least one smear preparing condition not in association with a range of hematocrit values but in association with a smearing levels; and
      a controller coupled to the spreader glass driving mechanism and the memory, wherein the controller is connected to the host computer via the network;
   wherein the host computer sends, to the smear preparing apparatus, the smearing level when the analysis results of the blood sample other than the hematocrit value meets a predetermined condition, and sends, to the smear preparing apparatus, the hematocrit value included in the analysis results when the analysis results other than the hematocrit value do not meet the predetermined condition;
   wherein when the controller receives the smearing level from the host computer, the controller controls the spreader glass driving mechanism according to a smear preparing condition stored in the memory in association with the received smearing level, and when the controller receives the hematocrit value from the host computer, the controller controls the spreader glass driving mechanism according to a smear preparing condition stored in the memory in association with the received hematocrit value.

2. The system of claim 1, wherein the memory further comprises a table associating each smear preparing condition with at least a range of hematocrit values or with a smearing level.

3. The system of claim 1, wherein the smear preparing condition comprises a condition from the following conditions: speed, angle, fitting time, amount of dispensed sample, and combinations thereof.

4. The system of claim 1, wherein the analysis results, other than the hematocrit value include a number of blood cells and an abnormal message generated by the blood sample analyzer.

5. The system of claim 1, wherein the smear preparing apparatus further comprises an input unit; and
   the memory stores a smear preparing conditions inputted through the input unit in association with the smearing levels.

6. The system of claim 5, wherein
   the memory stores smear preparing conditions modified through the input unit in association with the smearing levels.

7. The system of claim 1, wherein
   the memory stores predetermined smear preparing conditions in association with the ranges of hematocrit values.

8. The system of claim 1, wherein
   the analysis results of the blood sample other than the hematocrit value include a number of blood cells generated by the blood sample analyzer; and
   the host computer sends the smearing level when the number of the blood cells included in the analysis results falls within a predetermined range.

9. The system of claim 1, wherein
   the analysis results of the blood sample other than the hematocrit value include an abnormal message generated by the blood sample analyzer; and
   the host computer sends the smearing level when the abnormal message included in the analysis results indicates a predetermined abnormality.

10. The system of claim 9, wherein
    the predetermined abnormality is selected from white blood cell abnormality, neutropenia, neutrophilia, lymphopenia, lymphocytosis, red blood cell abnormality, anemia, red blood cell agglutination, hemoglobin defect and platelet abnormality.

* * * * *

UNITED STATES PATENT AND TRADEMARK OFFICE
CERTIFICATE OF CORRECTION

PATENT NO.        : 8,449,822 B2
APPLICATION NO.   : 11/407518
DATED             : May 28, 2013
INVENTOR(S)       : Masanori Nakaya et al.

It is certified that error appears in the above-identified patent and that said Letters Patent is hereby corrected as shown below:

In the Claims

In column 7, claim 1, line 65, after "with a smearing" replace "levels;" with --level;--.

Signed and Sealed this
Fifth Day of August, 2014

Michelle K. Lee
*Deputy Director of the United States Patent and Trademark Office*